United States Patent
Yoon et al.

(10) Patent No.: US 11,020,090 B2
(45) Date of Patent: Jun. 1, 2021

(54) METHOD AND ULTRASOUND APPARATUS FOR SETTING PRESET

(71) Applicant: SAMSUNG MEDISON CO., LTD., Gangwon-do (KR)

(72) Inventors: Ki-sang Yoon, Gangwon-do (KR); Dong-gyu Hyun, Gangwon-do (KR); Yong-soo Kim, Gangwon-do (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 1120 days.

(21) Appl. No.: 14/931,301

(22) Filed: Nov. 3, 2015

(65) Prior Publication Data

US 2016/0262726 A1    Sep. 15, 2016

(30) Foreign Application Priority Data

Mar. 9, 2015    (KR) .................. 10-2015-0032510

(51) Int. Cl.
| | |
|---|---|
| *A61B 8/00* | (2006.01) |
| *A61B 8/08* | (2006.01) |
| *A61B 8/14* | (2006.01) |
| *G06F 3/0482* | (2013.01) |
| *G06F 3/0484* | (2013.01) |

(52) U.S. Cl.
CPC ............ *A61B 8/467* (2013.01); *A61B 8/14* (2013.01); *A61B 8/4477* (2013.01); *A61B 8/463* (2013.01); *A61B 8/465* (2013.01); *A61B 8/5207* (2013.01); *A61B 8/585* (2013.01); *G06F 3/0482* (2013.01); *G06F 3/04842* (2013.01); *G06F 3/04847* (2013.01)

(58) Field of Classification Search
CPC ......... A61B 8/14; A61B 8/4477; A61B 8/463; A61B 8/465; A61B 8/467; A61B 8/461; A61B 8/469; A61B 8/54
See application file for complete search history.

(56) References Cited

U.S. PATENT DOCUMENTS

| | | | |
|---|---|---|---|
| 2003/0025676 A1* | 2/2003 | Cappendijk | ......... G06F 3/04886 345/173 |
| 2005/0080326 A1* | 4/2005 | Mathew | ............... A61B 5/1171 600/407 |
| 2006/0058654 A1 | 3/2006 | Di Marco et al. | |
| 2007/0232907 A1 | 10/2007 | Pelissier et al. | |

(Continued)

FOREIGN PATENT DOCUMENTS

| | | |
|---|---|---|
| JP | 2000-014670 A | 1/2000 |
| JP | 2000-107176 A | 4/2000 |

(Continued)

OTHER PUBLICATIONS

Extended European Search Report EP Application No. 15175923.0 dated Aug. 5, 2016.

*Primary Examiner* — Baisakhi Roy
(74) *Attorney, Agent, or Firm* — Morgan, Lewis & Bockius LLP

(57) ABSTRACT

Provided is a method of setting an ultrasound preset, which includes displaying a selection window on a screen for selecting the preset corresponding to the selected probe upon at an event of selecting the probe, and to hide the selection window, in the case a user input for selecting the preset corresponding to the selected probe is not entered within a reference time.

20 Claims, 18 Drawing Sheets

(56) References Cited

U.S. PATENT DOCUMENTS

| | | | |
|---|---|---|---|
| 2008/0269610 A1* | 10/2008 | Burla | A61B 8/00 600/447 |
| 2012/0226161 A1 | 9/2012 | Pelissier et al. | |
| 2014/0053111 A1* | 2/2014 | Beckman | G06F 3/04812 715/856 |
| 2014/0107487 A1 | 4/2014 | Kim et al. | |
| 2014/0180106 A1* | 6/2014 | Takahashi | A61B 8/585 600/443 |
| 2015/0331573 A1* | 11/2015 | Zhu | G06F 3/0481 715/800 |

FOREIGN PATENT DOCUMENTS

| | | |
|---|---|---|
| JP | 2014-057631 A | 4/2014 |
| KR | 10-2012-0059739 A | 6/2012 |

\* cited by examiner

FIG. 1B

| PROBE ID INFORMATION (110) | APPLICATION | PRESET ID INFORMATION (120) | |
|---|---|---|---|
| PA(Phased Array 2~4 Mhz) | Abdomen | Aorta | 205 |
| | | Renal | 210 |
| | | Liver | 215 |
| | Cardiac | Aorta | 220 |
| | | Pediactric | 225 |
| | | Liver | 230 |
| | Transcranial Doppler | TCD | 235 |
| EC(Endocavity 4~9 Mhz) | Obstetrics | 1st Trimester | |
| | Gynecology | Adnexa | |
| | | General | |
| | Urology | Prostate | |
| CV(Convex 5~8 Mhz) | Pediatric | Abdomen | 240 |
| | | Neonatal Head | 245 |
| | Vascular | Aorta | 250 |
| | | Pediactric | 255 |
| | | Liver | 260 |
| LN(Linear 7.5~10 Mhz) | . . . . | . . . . | |

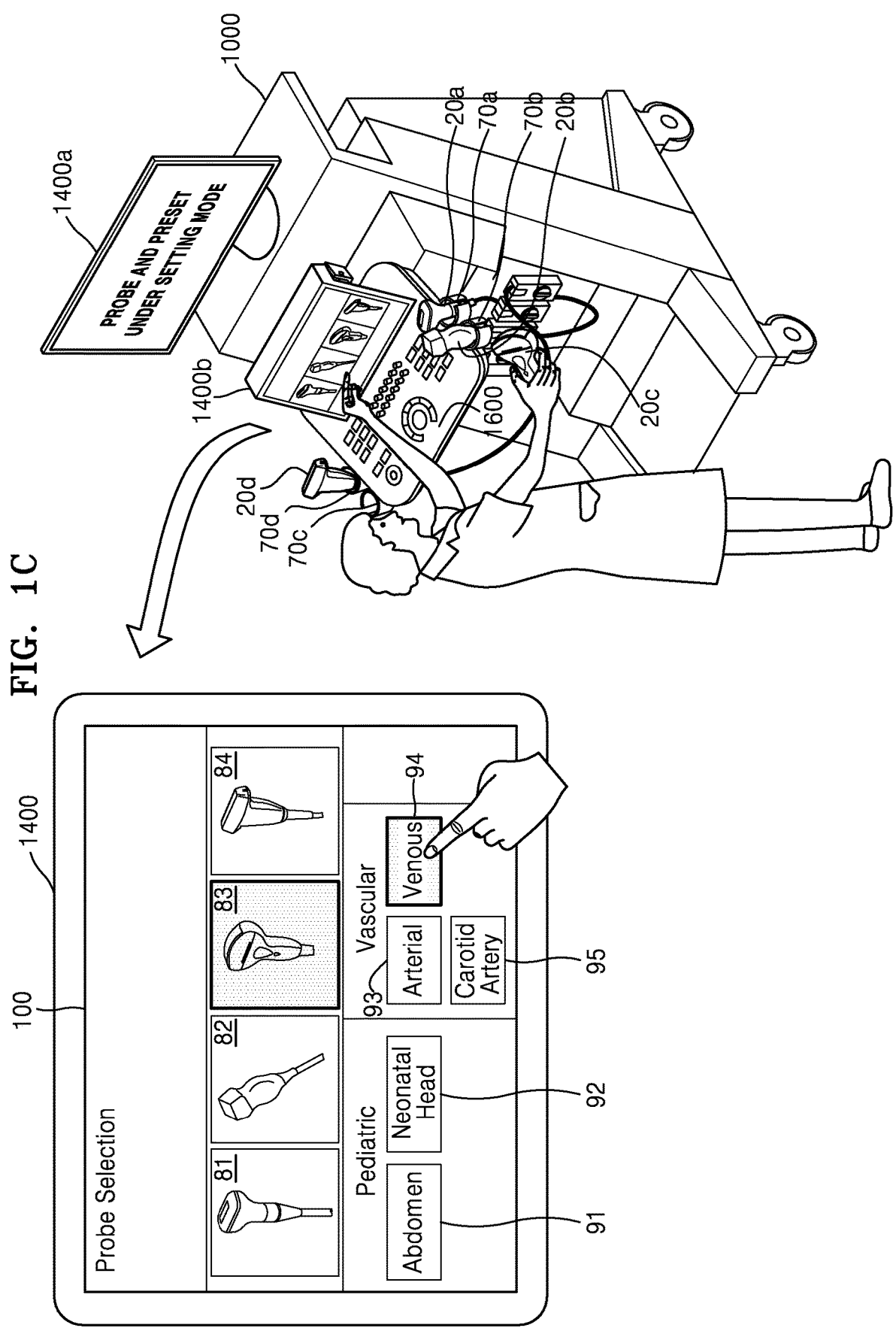

FIG. 3B

| PROBE ID INFORMATION | RFID ID INFORMATION |
|---|---|
| PA(Phased Array 2~4 Mhz) | a1209 |
| EC(Endocavity 4~9 Mhz) | b3479 |
| CV(Convex 5~8 Mhz) | c5658 |
| LN(linear 7.5~10 Mhz) | d7843 |

110 — PROBE ID INFORMATION
320 — RFID ID INFORMATION

FIG. 4B

| PRESET ID INFORMATION | MOST RECENTLY USED PRESET | MOST FREQUENTLY USED PRESET | PRESET DETERMINED BY USER |
|---|---|---|---|
| PA(Phased Array 2~4 Mhz) | Liver | Renal | Renal |
| EC(Endocavity 4~9 Mhz) | General | General | General |
| CV(Convex 5~8 Mhz) | Carotid Artery | Carotid Artery | Abdomen |

110  410  420  430

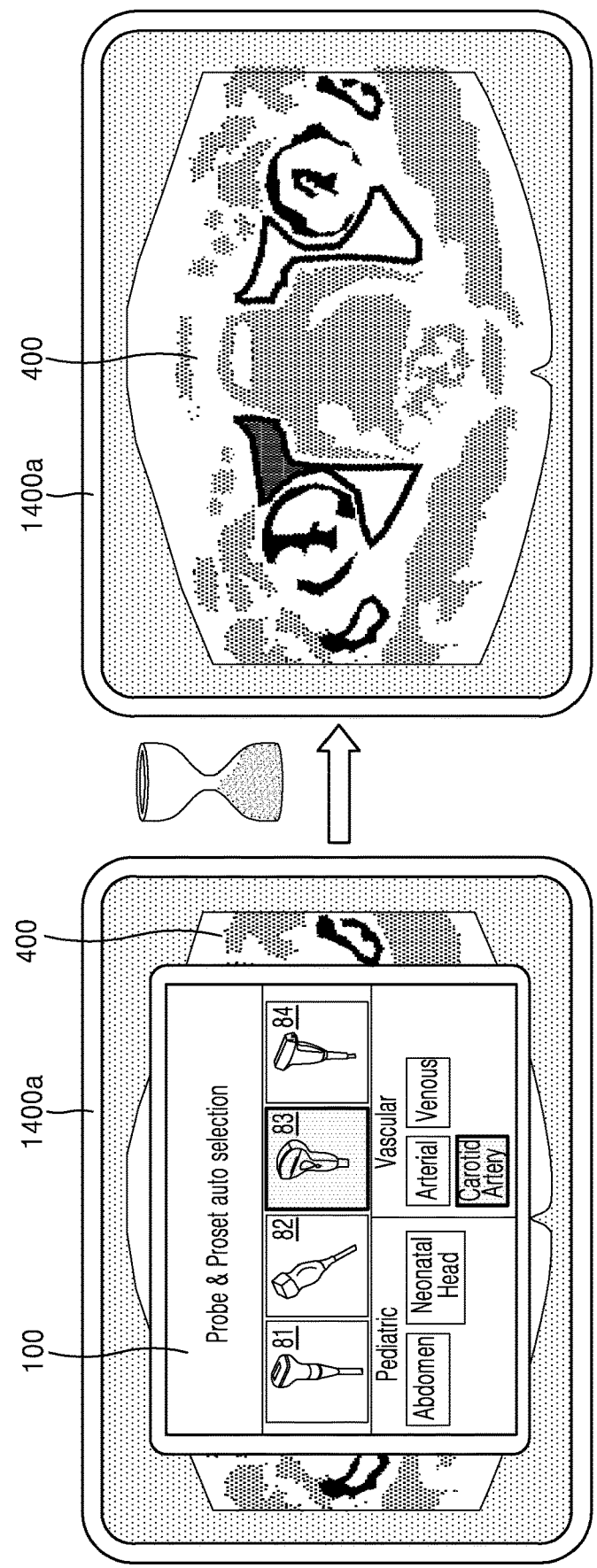

FIG. 7B

| PATIENT ID INFORMATION | PROBE ID INFORMATION | DEFAULT PRESET ID INFORMATION |
|---|---|---|
| PATIENT NO. 1 | PA(Phased Array 2~4 Mhz) | Liver |
|  | EC(Endocavity 4~9 Mhz) | Prostate |
| PATIENT NO. 2 | PA(Phased Array 2~4 Mhz) | Abdomen |

FIG. 7C

| TARGET REGION | PROBE ID INFORMATION | DEFAULT PRESET ID INFORMATION |
|---|---|---|
| LARGE INTESTINE | PA(Phased Array 2~4 Mhz) | Abdomen |
| THYROID GLAND | EC(Endocavity 4~9 Mhz) | Carotid Artery |

760 — TARGET REGION
770 — PROBE ID INFORMATION
780 — DEFAULT PRESET ID INFORMATION

METHOD AND ULTRASOUND APPARATUS FOR SETTING PRESET

CROSS-REFERENCE TO RELATED PATENT APPLICATION

This application claims the benefit of Korean Patent Application No. 10-2015-0032510, filed on Mar. 9, 2015, in the Korean Intellectual Property Office, the disclosure of which is incorporated herein in its entirety by reference.

BACKGROUND OF THE INVENTION

1. Field of the Invention

One or more exemplary embodiments relate to a method and an ultrasound imaging apparatus which automatically selects a preset, based on a user's use history of probes.

2. Description of the Related Art

Ultrasound imaging apparatuses transmit ultrasound signals generated by transducers of a probe to an object and receive echo signals reflected from the object, thereby obtaining at least one image of the inside of the object (e.g., soft tissue or blood flow). In particular, ultrasound imaging apparatuses are used for medical purposes including observation of the interior of an object, detection of foreign substances, and diagnosis of damage to the object. Such Ultrasound imaging apparatuses are highly reliable, display images in real time, and are safe due to the lack of radioactive exposure, compared to X-ray apparatuses. Therefore, Ultrasound imaging apparatuses are widely used together with other image diagnosis apparatuses including a computed tomography (CT) apparatus, a magnetic resonance imaging (MRI) apparatus, and the like.

Ultrasound imaging apparatuses may include various types of probes. A user selects one of a plurality of probes, and sets a parameter suitable for the selected probe and object into the ultrasound imaging apparatuses. In this case, the user selects the identifiable (ID) information of the probe intended to be used, and enters the parameter suitable for generating images into the ultrasound imaging apparatuses.

Therefore, much time is required to key in information when selecting parameters, because the user must select the ID information of the probe and enter the parameter suitable for generating images whenever the ultrasound imaging apparatuses are used.

SUMMARY OF THE INVENTION

One or more exemplary embodiments provide a method of automatically selecting a preset, based on a user's use history of probes.

Additional aspects will be set forth in part in the description which follows and, in part, will be apparent from the description, or may be learned by practice of the presented embodiments.

According to a primary aspect of exemplary embodiments, provided is a method of setting an ultrasound preset, which may include displaying, on a screen, a selection window for selecting a preset corresponding to an event of selecting a probe by a user, and hiding the selection window when a user input selecting a preset corresponding to the selected probe is not entered within a reference time.

In some embodiments, the reference time is set to a default value and is changeable by the user.

In some embodiments, the method of setting the ultrasound preset may further include, when a user input selecting a preset corresponding to the selected probe is entered within the reference time, activating the selected probe based on a preset selected.

In some embodiments, the preset corresponding to the probe selected may include a plurality of presets corresponding to the selected probe, and the method of setting an ultrasound preset may further include receiving the event of selecting the probe, and applying a preset to the selected probe, wherein the applied preset is selected from among the plurality of presets corresponding to the selected probe.

In some embodiments, the method of setting the ultrasound preset may further include generating an ultrasound image based on an echo signal received through the selected probe when the selected probe is activated, and displaying the generated ultrasound image.

In some embodiments, the displaying of the selection window on the screen may further include displaying, on the selection window, an identifier indicating that the selected probe is chosen to transmit and receive ultrasound signals, and displaying, on the selection window, an identifier indicating the applied preset.

In some embodiments, the applied preset may be a preset which was most recently used for the selected probe.

In some embodiments, the applied preset may be a preset which is used most frequently for the selected probe from among the plurality of presets.

In some embodiments, the applied preset may be a preset which has already been predetermined by a user for the selected probe.

In some embodiments, the applied preset may be a preset which corresponds to identifiable information about the object.

In some embodiments, the applied preset may be a preset which corresponds to identifiable information about the user.

In some embodiments, according to a primary aspect of exemplary embodiments, provided is an ultrasound imaging apparatus which may display a selection window on a screen for selecting a preset corresponding to a probe selected at an event of selecting the probe, and may hide the selection window, in the case a user input for selecting the preset corresponding to the selected probe is not entered within the reference time.

In some embodiments, the ultrasound imaging apparatus may include a user input unit and a controller. The user input unit may receive the user input to select a preset displayed within the reference time, and the controller may activate the selected probe, based on the selected preset upon receiving the user input to select the preset displayed within the reference time.

In some embodiments, the preset corresponding to the selected probe may include a plurality of presets. The user input unit may receive the event of selecting the probe, and the controller may activate the selected probe, based on a preset predetermined before the probe is selected corresponding to the selected probe, among the plurality of presets which correspond to the selected probe, at the event of selecting the probe.

In some embodiments, the ultrasound imaging apparatus may further include a display unit. The control unit may generate an ultrasound image based on an echo signal received through the probe when the selected probe is activated and the display unit displays the generated ultrasound image.

In some embodiments, the display unit may display that the selected probe is selected as a probe to transmit and receive ultrasound signals on the selection window, and also may display that the predetermined preset corresponding to the probe is selected among the plurality of presets corresponding to the selected probe on the selection window.

BRIEF DESCRIPTION OF THE DRAWINGS

These and/or other aspects will become apparent and more readily appreciated from the following description of the embodiments, taken in conjunction with the accompanying views of which:

FIGS. 1A to 1C are views illustrating a method in which an imaging probe and an imaging preset are selected on an ultrasound imaging apparatus, according to an embodiment of the present invention;

FIGS. 3A and 3B are views illustrating the method in which the ultrasound imaging apparatus selects an imaging probe automatically based on the movement of a probe according to an embodiment of the present invention;

FIGS. 4A and 4B are views illustrating the method in which the ultrasound imaging apparatus automatically selects a preset to be used as the imaging parameter according to an embodiment of the present invention;

FIGS. 5A and 5B are views illustrating the method in which the ultrasound imaging apparatus displays a selection window according to an embodiment of the present invention;

FIGS. 7A, 7B and 7C are views illustrating the method in which the ultrasound imaging apparatus sets the imaging parameter based on the ID information of the object according to an embodiment of the present invention;

DETAILED DESCRIPTION

Figure 1A:
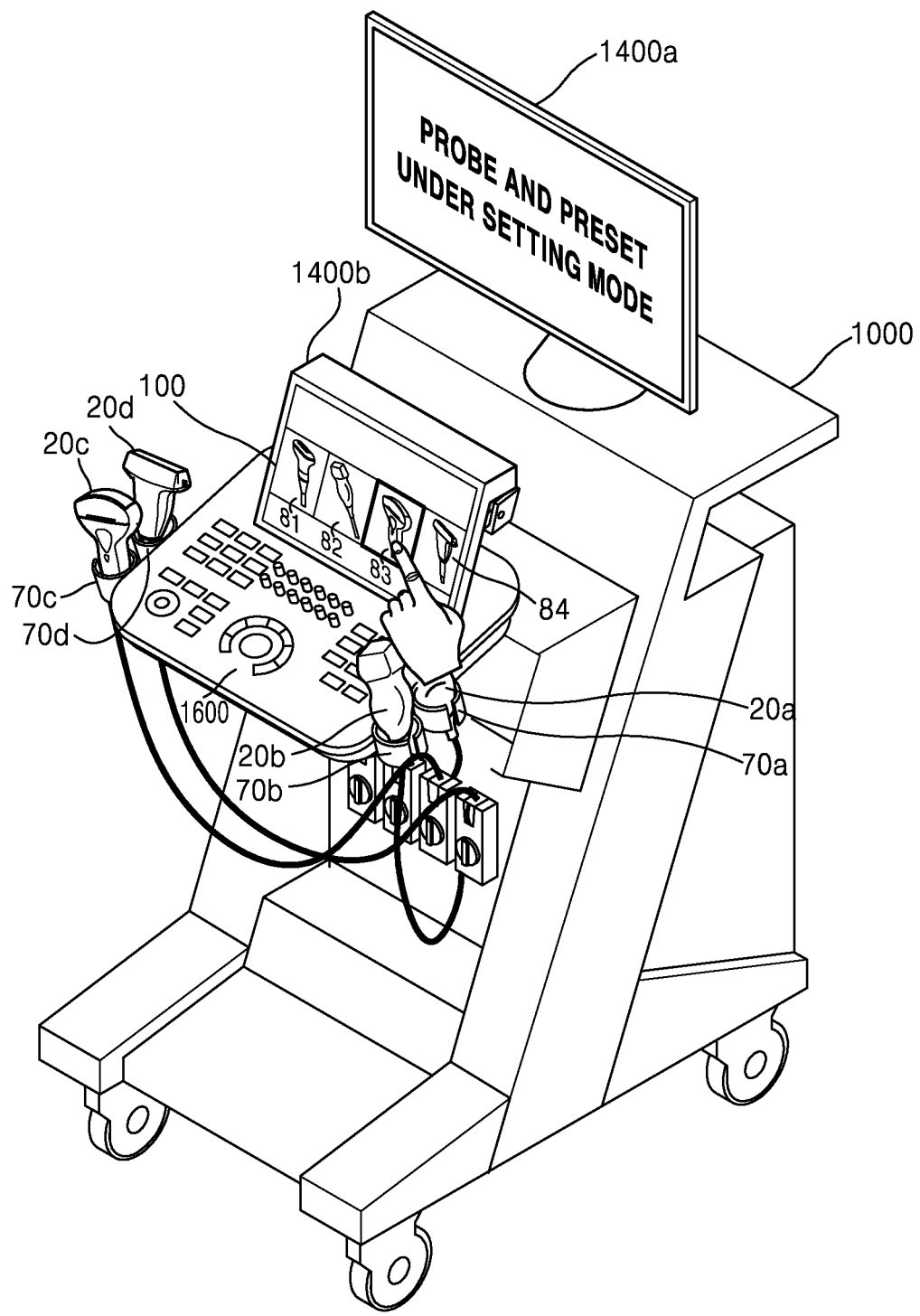

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

Terms used for the present invention are the terms which are used as commonly and widely as possible, while considering functions of the terms in the present invention. However, the terms may be altered depending on what engineers involved in the field intend to mean, any precedents and the advent of new technologies. Also, some terms may be arbitrarily selected by the applicant, and in this case, the meaning of the selected terms will be described in detail in the detailed description of the present specification. Therefore, the terms used for the present invention is defined considering the possible meanings of the terms and their application for the invention, rather than the conventional and literal meanings of the terms.

Throughout the specification, it will also be understood that when a component "includes" an element, unless clearly stated otherwise, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may include at least one of the followings: organs such as the liver, heart, uterus, brain, breasts, and abdomen, and blood vessels. Also, the object may be a phantom. A phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Hereinafter, exemplary embodiments of the present invention will be explained in detail by referring to the attached drawings.

FIG. 1 is a view illustrating how an ultrasound imaging apparatus 1000 selects an imaging probe and an imaging preset according to an embodiment of the present invention.

Referring to FIG. 1, the ultrasound imaging apparatus 1000 may include a main display unit 1400a, a sub-display unit 1400b, a user input unit 1600, probes 20a-20d and probe holders 70a-70d.

The main display unit 1400a may display an ultrasound image while the sub-display unit 1400b may display a user interface, but the display units are not limited thereto. As shown in FIG. 1A, the main display unit 1400a and the sub-display unit 1400b may be implemented as dual screens or a single screen according to an embodiment of the present invention. In case one or both of the main display unit 1400a and the sub-display unit 1400b includes a touch panel, the main display unit 1400a and the sub-display unit 1400b may also be used as a user input unit such as a touch screen.

The probes 20a-20d may respectively be a Phased Array Probe, an Endocavity Probe, a convex probe, and a Linear Probe, but are not limited thereto.

The probes 20a-20d may be stored in probe holders 70a-70d, respectively. The probe holders 70a-70d may be mounted to the ultrasound imaging apparatus 1000. For example, the probe holders 70a-70d may be mounted to sides of the control panel 1600.

Each of the probes 20a-20d may be connected to the ultrasound imaging apparatus 1000 via a cable. In some embodiments, each of the probes 20a-20d may be connected to the ultrasound imaging apparatus 1000 wirelessly.

The ultrasound imaging apparatus 1000 may display a selection window 100. A user may select one of the probes 20a-20d as an imaging probe and select one of a plurality of presets corresponding to the selected probe as an imaging parameter via the selection window 100.

An imaging probe may refer to one of the probes 20a-20d which is activated while imaging ultrasound images. When one of the probes 20a-20d is selected as the imaging probe, the ultrasound imaging apparatus 1000 may apply a voltage pulse to the imaging probe and thereby may transmit and receive an ultrasound signal.

An imaging parameter may refer to the parameter which is set on the ultrasound imaging apparatus 1000 when it is used in generating an ultrasound image. Depending on the region of imaging or the status of the object, the target region may vary in depth from the skin, size, the types of tissue and a display method. Therefore, depending on the region of imaging or the status of the object, parameters may vary, such as in-pulse repeat frequency, reception frequency of ultrasound echo signals, pulse length of ultrasound pulses, coding method of ultrasound pulses, gain, line density, number of lines, depth of focal point, parameter of wall filter, resolution of ultrasound images, frame rate or user interface.

Accordingly, a set of parameters suitable for the corresponding types of probes 20a-20d, the region of imaging or the status of the object may be preset for the ultrasound imaging apparatus 1000. The set of parameters pre-stored for the corresponding types of probes 20a-20b, the region of imaging or the status of the object may be referred to as a "preset." The preset may be stored beforehand in the ultrasound imaging apparatus 1000 by the manufacturer of the ultrasound imaging apparatus 1000. In some embodiments, the preset may be received from an external device or generated by the user.

As shown in FIG. 1B, preset identification (ID) information 120 corresponding to probe ID information 110 may be stored in the ultrasound imaging apparatus 1000. For example, seven presets corresponding to a phased array probe 20a may be stored for tests of abdominal aorta 205, abdomen renal 210, abdomen liver 215, cardiac aorta 220, cardiac pediactric 225, cardiac liver 230 and transcranial doppler (TCD) 235.

Referring to FIG. 1A again, the selection window 100 may include a plurality of probe selection buttons 81 through 84. The probe selection buttons 81 through 84 may be respectively assigned to the probes 20a to 20d which are connected to the ultrasound imaging apparatus 1000. The ultrasound imaging apparatus 1000 may receive a user input for selecting one of the probe selection buttons 81 through 84. For example, the ultrasound imaging apparatus 1000 may receive the user input for selecting one of the probe selection buttons 81 through 84 via a trackball mounted to the control panel. In some embodiments, the ultrasound imaging apparatus 1000 may receive the user input for selecting one of the probe selection buttons 81 through 84 via a touch input on the screen of the display 1400.

Referring to FIG. 1C, as the user enters the user input for selecting one of the probe selection buttons 81 through 84, the ultrasound imaging apparatus 1000 may designate probes 20a-20b corresponding to the selected probe selection button as the imaging probe. In some embodiments, the ultrasound imaging apparatus 1000 may display the preset selection buttons 91 through 95 for the user to select one of the presets corresponding to the designated imaging probe.

For example, the ultrasound imaging apparatus 1000 may acquire a plurality of preset IDs corresponding to a convex probe, upon receiving the user input for selecting the convex probe selection button 83 from among the probe selection buttons 81 through 84.

Referring to FIG. 1B, the ultrasound imaging apparatus 1000 may have five presets stored corresponding to a convex probe, including abdomen 240, neonatal head 245, arterial 250, carotid artery 255, and liver 260.

Upon receiving the above five presets corresponding to a convex probe, the ultrasound imaging apparatus 1000 may display five preset selection buttons 91 through 95 in the selection window 100. In this case, the ultrasound imaging apparatus 1000 may display each preset ID on each of preset selection buttons 91 through 95.

The ultrasound imaging apparatus 1000 may receive the user input for selecting one of the preset selection buttons 91 through 95. Upon receiving the user input for selecting one of the preset selection buttons 91 through 95, the ultrasound imaging apparatus 1000 may designate the preset corresponding to the selected preset selection button as an imaging parameter. In some embodiments, the ultrasound imaging apparatus 1000 may apply a voltage pulse to the selected probe based on a determined the imaging parameter, and generate an ultrasound image based on an echo signal reflected from the object.

For example, the ultrasound imaging apparatus 1000 may transmit an ultrasound signal through a convex probe based on the parameter value of the "Venous" preset, and may generate an ultrasound image based on the echo signal reflected from the object, upon receiving the user input for selecting the "Venous" preset selection button 94 among the preset selection buttons 91 through 95.

FIG. 1A through FIG. 1C illustrate an embodiment in which the user enters the user input for selecting the imaging probe and the imaging preset into the ultrasound imaging apparatus. However, the present exemplary embodiment is not limited thereto. The ultrasound imaging apparatus 1000 may automatically select the imaging probe and the imaging preset.

Figure 2:
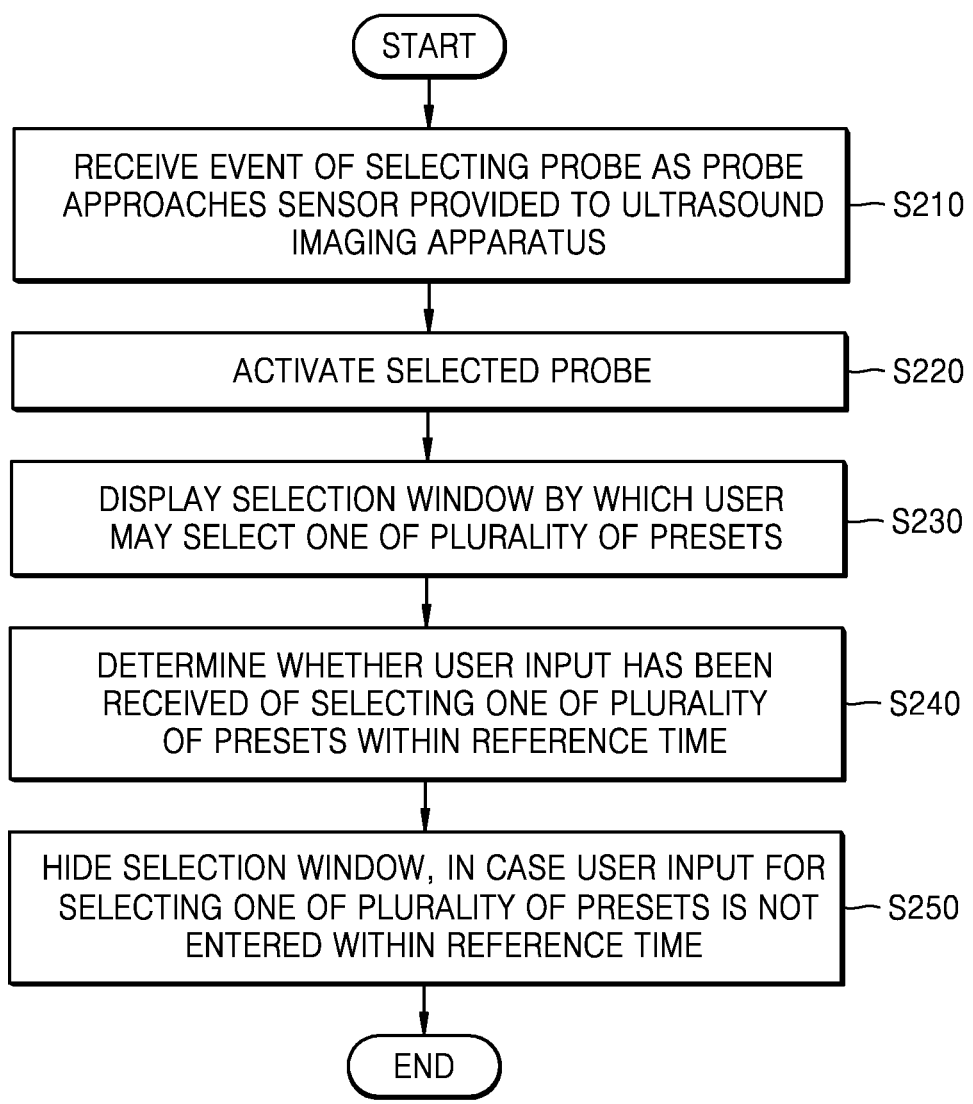
FIG. 2 is a flowchart illustrating the method in which the ultrasound imaging apparatus sets probes and presets automatically according to an embodiment of the present invention.

FIG. 2 is a flowchart illustrating the method in which the ultrasound imaging apparatus may set the probe and preset automatically according to an embodiment of the present invention.

In operation S210, the ultrasound imaging apparatus 1000 may receive the event of selecting the probe as the probe approaches a sensor unit included in the ultrasound imaging apparatus 1000.

"The event of selecting the probe" may refer to an event in which the ultrasound imaging apparatus 1000 detects the selection of a probe by using the sensor included in the ultrasound imaging apparatus 1000.

The event of selecting the probe may include: the event in which the user removes the probe from the probe holder; the event in which the probe is held by the user; and the event of selecting the probe by moving the probe toward the control panel or the sensor unit included in the ultrasound imaging apparatus 1000, but is not limited thereto. The sensor unit may include an RFID reader and an RFID antenna. The RFID antenna may be mounted inside the control panel while remaining separate from the RFID reader.

The ultrasound imaging apparatus 1000 may recognize the user input for selecting the probe, since the probe approaching the sensor unit of the ultrasound imaging apparatus 1000 indicates that the probe is being removed from the probe holder.

For example, the ultrasound imaging apparatus 1000 may be furnished with a sensor which may recognize each probe. For example, each probe may be furnished with an RFID tag. In some embodiments, the ultrasound imaging apparatus 1000 may be furnished with an RFID antenna which receives the probe identifiable (ID) information from the RFID tag and the RFID reader which recognizes the probe ID information. When the probe is near each of the antennae mounted inside the ultrasound imaging apparatus 1000, one of the RFID readers may identify the probe ID information received through the RFID tag located on the approaching probe.

As the ultrasound imaging apparatus 1000 identifies the probe ID information from the RFID tag which is located on the approaching probe, the ultrasound imaging apparatus 1000 may produce an event which indicates that the probe has been removed from the probe holder. As the event occurs which indicates that the probe has been removed from the probe holder, the ultrasound imaging apparatus 1000 may recognize that the probe corresponding to the ID information has been selected.

In operation S220, the ultrasound imaging apparatus 1000 may activate the selected probe.

For example, the ultrasound imaging apparatus 1000 may activate the selected probe, based on the predetermined preset among the presets which correspond to the selected probe. The preset predetermined before the probe is selected may be a preset selected by the user or a default preset set by the manufacturer of the ultrasound imaging apparatus 1000.

The preset determined before the selection of the probe may be referred to as a default preset. The ultrasound imaging apparatus 1000 may have a default preset which corresponds to the probe ID information. The default preset may refer to the preset which is automatically set as the imaging parameter when the probe is set as the imaging probe among the presets.

The default preset which corresponds to the probe may be the preset most recently used among the presets. In some embodiments, the default preset which corresponds to the probe may be the preset most frequently used among the presets. In some embodiments, the default preset which corresponds to the probe may be the preset already determined by the user from among the presets.

In some embodiments, the default preset corresponding to the probe may be the preset which corresponds to the ID information of an object. In some embodiments, the default preset corresponding to the probe may be the preset which corresponds to the ID information of the user.

When the default preset is automatically selected as the imaging parameter, the ultrasound imaging apparatus 1000 may indicate in the selection window that the default preset has automatically been selected as the imaging parameter.

In some embodiments, when the default preset is automatically selected as the imaging parameter, the ultrasound imaging apparatus 1000 may activate the probe based on the default preset. When the probe is activated, the ultrasound imaging apparatus 1000 may receive an ultrasound echo signal reflected from the object through the probe, and generate an ultrasound image based on the echo signal. In some embodiments, the ultrasound imaging apparatus 1000 may display the generated ultrasound image.

In operation S230, the ultrasound imaging apparatus 1000 may display on the screen of the ultrasound imaging apparatus the selection window by which the user may select one of the presets.

The ultrasound imaging apparatus 1000 may display on the screen of the ultrasound imaging apparatus the selection window by which the user may select one of the presets corresponding to the selected probe. In this case, the ultrasound imaging apparatus 1000 may indicate in the selection window that the selected probe has been chosen as the imaging probe to transmit and receive the ultrasound signal. In some embodiments, the ultrasound imaging apparatus 1000 may indicate in the selection window that the predetermined preset corresponding to the probe selected among the presets is selected.

In operation S240, the ultrasound imaging apparatus 1000 may determine whether the user input has been entered for selecting one of the presets within a reference time.

In operation S250, the ultrasound imaging apparatus 1000 may hide the selection window, in the case that the ultrasound imaging apparatus determines that the user input of selecting one of the presets has not been entered within a reference time.

According to an embodiment of the present invention, the ultrasound imaging apparatus 1000 may make the selection window invisible from the screen after selecting the predetermined preset, in the case that the ultrasound imaging apparatus determines that the user input of selecting one of the plurality of presets has not been entered within the reference time.

Figure 3A:
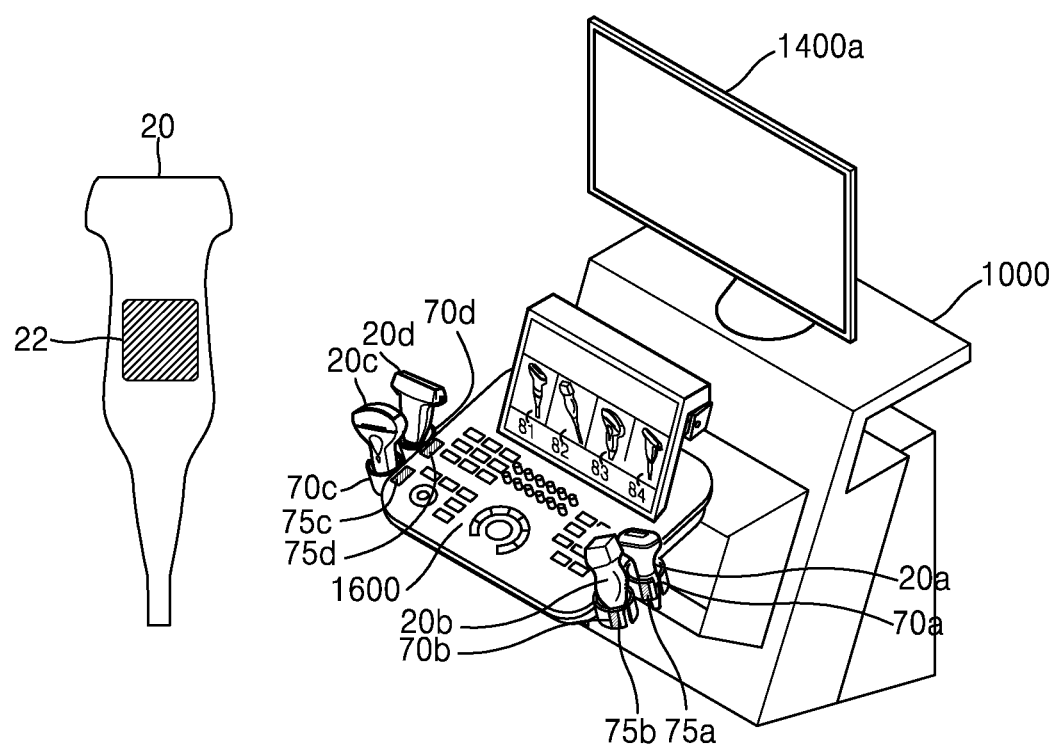

FIG. 3A and FIG. 3B are views illustrating the method in which the ultrasound imaging apparatus 1000 may select the imaging probe automatically based on a user's use history of probes, according to an embodiment of the present invention.

Referring to FIG. 3A, by using the RFID, the ultrasound imaging apparatus 1000 may identify which of the probes 20a-20d has been removed from one of the probe holders 70a-70d.

Each of the probes 20a-20d may be furnished with an RFID tag 22. For example, probe 20, which may represent any of the probes 20a-20d, is shown furnished with an RFID tag 22. In some embodiments, the ultrasound imaging apparatus 1000 may be furnished with an antenna which reads the ID information of the RFID 22, and the RFID reader which identifies the ID information of the RFID tag 22 received from the antenna 75. For example, the antennae 75a-75d may respectively be furnished to the probe holders 70a-70d. In some embodiments, a plurality of antennae 75a-75d may be mounted inside the control panel 1600.

In some embodiments, referring to FIG. 3B, the ultrasound imaging apparatus 1000 may save the ID information 320 included in the RFID 22 attached to the probe 20. That is, the ultrasound imaging apparatus 1000 may save ID information included in RFIDs respectively attached to the probes 20a-20d. For example, the ultrasound imaging apparatus 1000 may save the ID information of a Phased Array probe 20a as "PA". In some embodiments, the ultrasound imaging apparatus 1000 may save "a1209" which is the ID information 320 of the RFID 22 included in the RFID 22 of the Phased Array probe 20a, in correspondence with "PA".

The ultrasound imaging apparatus 1000 may regularly determine which of the antennae 70a-70d reads the ID information of the RFID tag 22. In the case in which one of the probes 20a-20d is removed from one of the probe holders 70a-70d, the antennae 75a-75d may be unable to read the RFID ID information of the withdrawn probe. In this case, the ultrasound imaging apparatus 1000 may determine that one of the probes 20a-20d corresponding to the ID information of the unread RFID tag was removed from one of the probe holders 70a-70d, based on the ID information of the unread RFID tag.

For example, in the case that the RFID ID information read by the antennae 75b-75d are "b3479", "c5658" and "d7843", the ultrasound imaging apparatus 1000 may determine that the Phased Array probe 20a, which is among the probes 20a-20d and corresponds to the unread ID information "a1209", has been removed from one of the probe holders, i.e., from probe holder 70a.

In some embodiments, each of the probes 20a-20d may be furnished with a Hall sensor, according to an embodiment of the present invention. In some embodiments, each of the probe holders 70 may be furnished with a magnetic field generator or a permanent magnet. In some embodiments, the probes 20 may transmit the information on Hall voltage measured by the Hall sensor to the controller of the ultrasound imaging apparatus 1000. In this case, the probe 20 may also transmit the ID information of the RFID tag attached to the probe 20.

While the probes 20a-20d are stored in the probe holders 70a-70d, Hall voltage of each of the probes 20a-20d may remain consistently stable. Again referring to probe 20, which may represent any of the probes 20a-2d, when the user moves the probe 20, the movement of the probe 20 may change the Hall voltage inside the Hall sensor inside of the probe 20. When the Hall voltage of a probe, for example, probe 20, increases beyond its allowed voltage, the probe 20 may transmit to the controller of the ultrasound imaging apparatus 1000 an event indicating that the probe 20 is selected. In this case, the probe 20 may also transmit the ID information of the probe 20 itself. Upon registering the event that one of the probes 20a-20d has been selected, the ultrasound imaging apparatus 1000 may determine which one of the probes 20a-20d has been removed, and from which of the probe holders 70a-70d, based on the received ID information of the probes 20a-20d.

In some embodiments, one of the probes 20a-20d may be furnished with an acceleration sensor which detects the movement of the probes 20a-20d, a Tilt sensor which detects the tilt of the probes 20a-20d, a position sensor which detects the position of the probes 20a-20d, a posture sensor which detects the posture or angular velocity of the probes 20a-20d. The position sensor may include an ElectroMagnetic sensor. In some embodiments, the posture sensor may include a gyro sensor or a GeoMagnetic sensor.

Again, the probe 20 may represent any of the probes 20a-20d. As the probe 20 is moved, a sensor mounted inside the probe 20 may transmit the information on the movement of the probe 20 to the controller of the ultrasound imaging apparatus 1000. In this case, the probe 20 may transmit the ID information of the probe 20 itself. The ultrasound imaging apparatus 1000 may determine whether any of the probes 20a-20d have been removed from or stored in one of the probe holders 70a-70d based on the information on the movement of the probes 20a-20d.

In some embodiments, the ultrasound imaging apparatus 1000 may be furnished with a camera to detect the positions of the probes 20, according to an embodiment of the present information. The ultrasound imaging apparatus 1000 may determine whether any of the probes 20a-20d has been removed from the probe holders 70a-70d by using the camera.

In some embodiments, the ultrasound imaging apparatus 1000 may detect a gesture of a user who is holding any of the probes 20a-20d, according to an embodiment of the present information. For example, the probe 20 may be furnished with a button which the user presses when the user holds the probe 20. When the user holds the probe 20 and presses the button affixed to the probe 20, the probe 20 may transmit to the controller of the ultrasound imaging apparatus 1000 information indicating that the button is pressed. In this case, the probe 20 may transmit the ID information of the probe 20 itself.

Figure 4A:
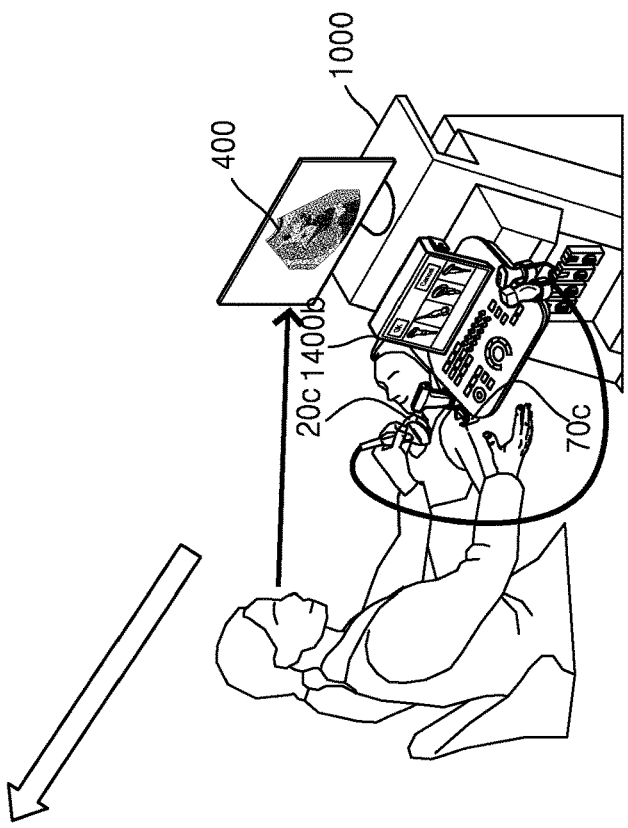
Figure 4A:
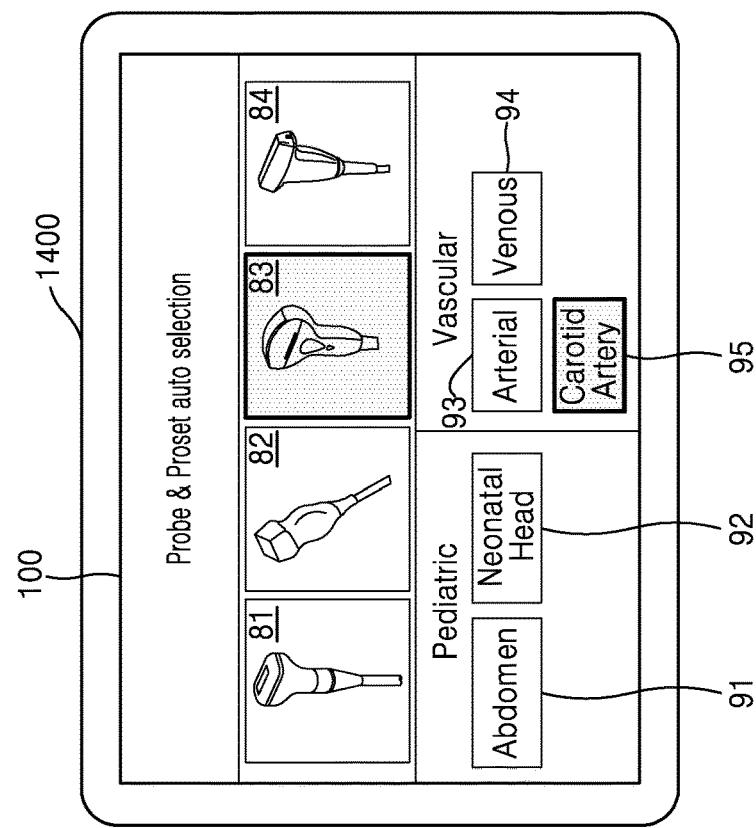

FIGS. 4A and 4B are views illustrating the method in which the ultrasound imaging apparatus may automatically select the preset to be used as the imaging parameter according to an embodiment of the present invention.

Referring to FIG. 4A, with the probe 20c automatically selected as the imaging probe, the ultrasound imaging apparatus 1000 may select as the imaging parameter the default preset corresponding to the selected probe 20c.

For example, when the user removes the probe 20c from the probe holder 70c, the ultrasound imaging apparatus 1000 may select the withdrawn probe 20c as the imaging probe. In some embodiments, the ultrasound imaging apparatus 1000 may indicate in the selection window 100 that the withdrawn probe 20c has been selected as the imaging probe. For example, the ultrasound imaging apparatus 1000 may indicate in the selection window 100 that the probe selection button corresponding to the withdrawn probe 20c needs to be pressed.

For example, as the user removes the convex probe 20c from one of the probe holders 70a-70d, e.g., probe holder 70c, the ultrasound imaging apparatus 1000 may determine the convex probe 20c as the imaging probe. By selecting the convex probe 20c as the imaging probe, the ultrasound imaging apparatus 1000 may display that the convex probe selection button 83 signifying the convex probe 20c needs to be pressed.

Referring to FIG. 4B, the ultrasound imaging apparatus 1000 may have the default preset saved in correspondence to the ID information 110 of the convex probe 20c. The default preset may refer to the preset which is automatically set by the ultrasound imaging apparatus 1000 as the imaging parameter from among the presets, when the convex probe 20c is selected as the imaging probe.

The default preset which corresponds to one of the probes 20a-20d may be the preset 410, which was used for capturing the most recent ultrasound image from among the presets corresponding to probes 20. In other words, the default preset may be the preset 410, which was selected most recently from among the presets corresponding to the probes 20. In some embodiments, the default preset which corresponds to the probes 20 may be the preset which has been the most frequently used for imaging ultrasound images among the presets corresponding to probes 20 during a certain period of time. In some embodiments, the default preset which corresponds to probes 20 may be the preset determined by the user from among the presets corresponding to probes 20. For example, the ID information of the preset which has been most frequently used and the ID information of the preset which was most recently used corresponding to the convex probe 20c may be "Carotid Artery". In some embodiments, the ID information of the preset which has been set by the user corresponding to the convex probe 20c may be "abdomen".

When saving the default preset, the ultrasound imaging apparatus 1000 may save the ID information of the preset which has been selected manually or automatically during the capture of the ultrasound image, with the information assigned to each of the probes 20a-20d. In this case, the ultrasound imaging apparatus 1000 may save the ID information of the preset along with information indicating the date and time when the preset is set. In some embodiments, the ultrasound imaging apparatus 1000 may calculate and determine which of the presets corresponding to probes 20 is the most frequently used during a certain period of time.

In some embodiments, the ultrasound imaging apparatus 1000 may provide a user interface for selecting, for each of the probes 20a-20d, a default preset selected from among the preset which has been most frequently used, the preset which was most recently used and the preset which was determined by the user.

Referring to FIG. 4A again, as the probe 20c which has been removed from the probe holder 70c is automatically determined as the imaging probe, the ultrasound imaging apparatus 1000 may determine the default preset as the imaging parameter among the presets which correspond to the selected probe 20.

For example, in the case that the convex probe 20c is automatically selected as the imaging probe, the ultrasound imaging apparatus 1000 may determine as the imaging parameter the default preset which corresponds to the convex probe 20c.

With the default preset automatically selected as the imaging parameter, the ultrasound imaging apparatus 1000 may indicate in the selection window 100 that the default preset has been automatically selected as the imaging parameter. For example, in the case that the "Carotid Artery" preset is predetermined as the default preset among the presets corresponding to the probe 20c, the ultrasound imaging apparatus 1000 may display that the preset selection button 95 signifying the "Carotid Artery" preset needs to be pressed.

In some embodiments, with the default preset automatically selected as the imaging parameter, the ultrasound imaging apparatus 1000 may activate the probe 20, based on the default preset. For example, the ultrasound imaging apparatus 1000 may apply the voltage pulse to the transducer mounted inside the convex probe 20c, based on pulse repeat frequency, pulse length of ultrasound pulse, coding method of ultrasound pulse, line density and number of lines which are saved in correspondence with the "Carotid Artery" preset. As the voltage pulse is applied to the transducer which is mounted inside the convex probe 20c, the transducer may transmit the ultrasound signal to the object. In some embodiments, the ultrasound imaging apparatus 1000 may receive the ultrasound echo signal reflected from the object through the convex probe 20c, and may also generate the ultrasound image 400 based on the ultrasound echo signal.

Accordingly, the user may set or change applications or presets just by removing one of the probes 20a-20d from the corresponding probe holders 70a-70d, without using the control panel or displayed user interface to manually select which of the probes 20a-20d will be used as the imaging probe, or selecting as the imaging parameter one of the presets corresponding to the imaging probe.

As the applications and presets are automatically set, the simple motion of removing one of the probes 20a-20d from each corresponding probe holders 70 is enough for the ultrasound imaging apparatus 1000 to generate the ultrasound image for the object and to display the generated ultrasound image on the screen.

Figure 5A:
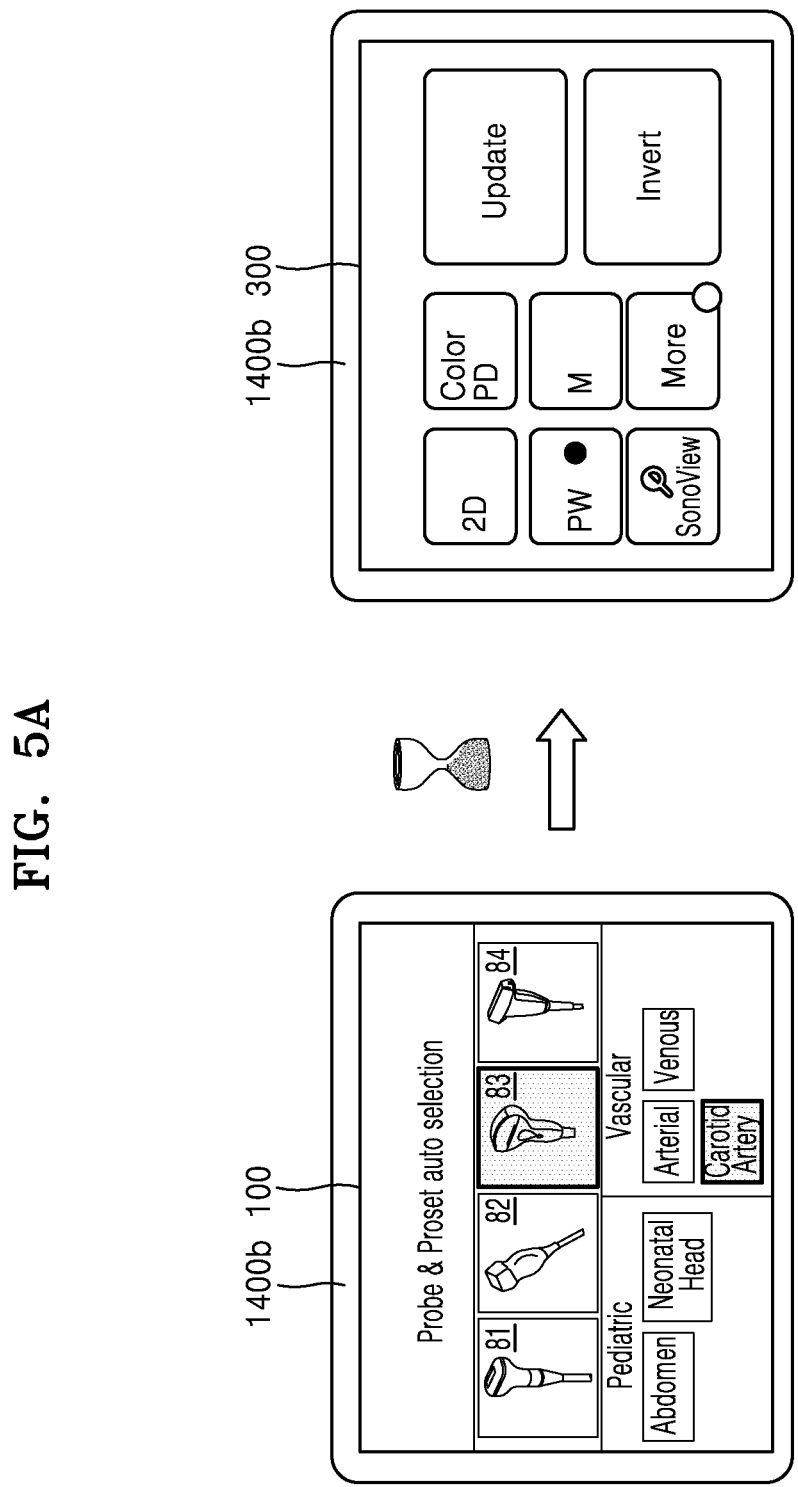

FIGS. 5A and 5B are views illustrating the method in which the ultrasound imaging apparatus displays a selection window according to an embodiment of the present invention.

Referring to FIG. 5A, the ultrasound imaging apparatus 1000 may display the selection window 100 on the screen and hide the selection window, in the case that the user input for selecting one of the presets is not entered within a reference time.

For example, the ultrasound imaging apparatus 1000 may display the selection window 100 on a sub display unit 1400b. In some embodiments, upon receiving the user input of removing any of the probes 20a-20d from one of the probe holders 70a-70d, the ultrasound imaging apparatus 1000 may determine the withdrawn probe 20 as the imaging probe, and determine the default preset corresponding to the determined probe 20 as the imaging parameter.

In some embodiments, the ultrasound imaging apparatus 1000 may indicate in the selection window 100 that the detected probe 20 and the default preset which corresponds to the detected probe 20 have been selected as the imaging probe and the imaging parameter, respectively. In some embodiments, the ultrasound imaging apparatus 1000 may use a recorded voice message to inform the user that the detected probe 20 and the default preset which corresponds to the detected probe 20 have been selected as the imaging probe and the imaging parameter, respectively.

Starting from the point when the ultrasound imaging apparatus 1000 respectively selects the detected probe 20 and the default preset which corresponds to the detected probe 20 as the imaging probe and the imaging parameter, the ultrasound imaging apparatus 1000 may determine whether a user input of changing the imaging probe or the imaging preset has been entered within a reference time.

In the case that the ultrasound imaging apparatus 1000 determines that a user input of changing the imaging probe or the imaging preset has not been entered within a reference time, the ultrasound imaging apparatus 1000 may make the selection window 100 displayed on the screen invisible and display another user interface 300 on the screen. For example, the ultrasound imaging apparatus 1000 may replace the selection window 100 displayed on the screen with a settings menu 300 for adjusting the display mode of displayed ultrasound images.

Referring to FIG. 5B, in the case that the user input has not been recognized for changing the imaging probe or the imaging preset within a reference time, the ultrasound imaging apparatus 1000 may hide the selection window 100.

For example, as the user removes the probe 20 from the probe holder 70 (i.e., removes one of the probes 20a-20d from one of the probe holders 70a-70d), the ultrasound imaging apparatus 1000 may acquire the default preset corresponding to the withdrawn probe 20, and generate the ultrasound image 400 based on the acquired default preset. The ultrasound imaging apparatus 1000 may display the generated ultrasound image 400 on the main display unit 1400a. In some embodiments, the ultrasound imaging apparatus 1000 may display the selection window 100 over the displayed ultrasound image 400. In this case, the ultrasound imaging apparatus 1000 may indicate in the selection window 100 that the detected probe 20 and the default preset which corresponds to the detected probe 20 have been selected as the imaging probe and the imaging parameter, respectively.

Starting from the moment of the display that the detected probe 20 and the default preset which corresponds to the detected probe 20 have been selected as the imaging probe and the imaging parameter, the ultrasound imaging apparatus 1000 may determine whether the user input has been received for changing the imaging probe or the imaging preset within a reference time.

In the case that the user input has not been entered for changing the imaging probe or the imaging preset within a reference time, the ultrasound imaging apparatus 1000 may make the selection window 100 displayed on the screen invisible and display only the ultrasound image 400 on the main display unit 1400*a*.

The reference time may be set by the user and is changeable by the user.

Figure 6A:
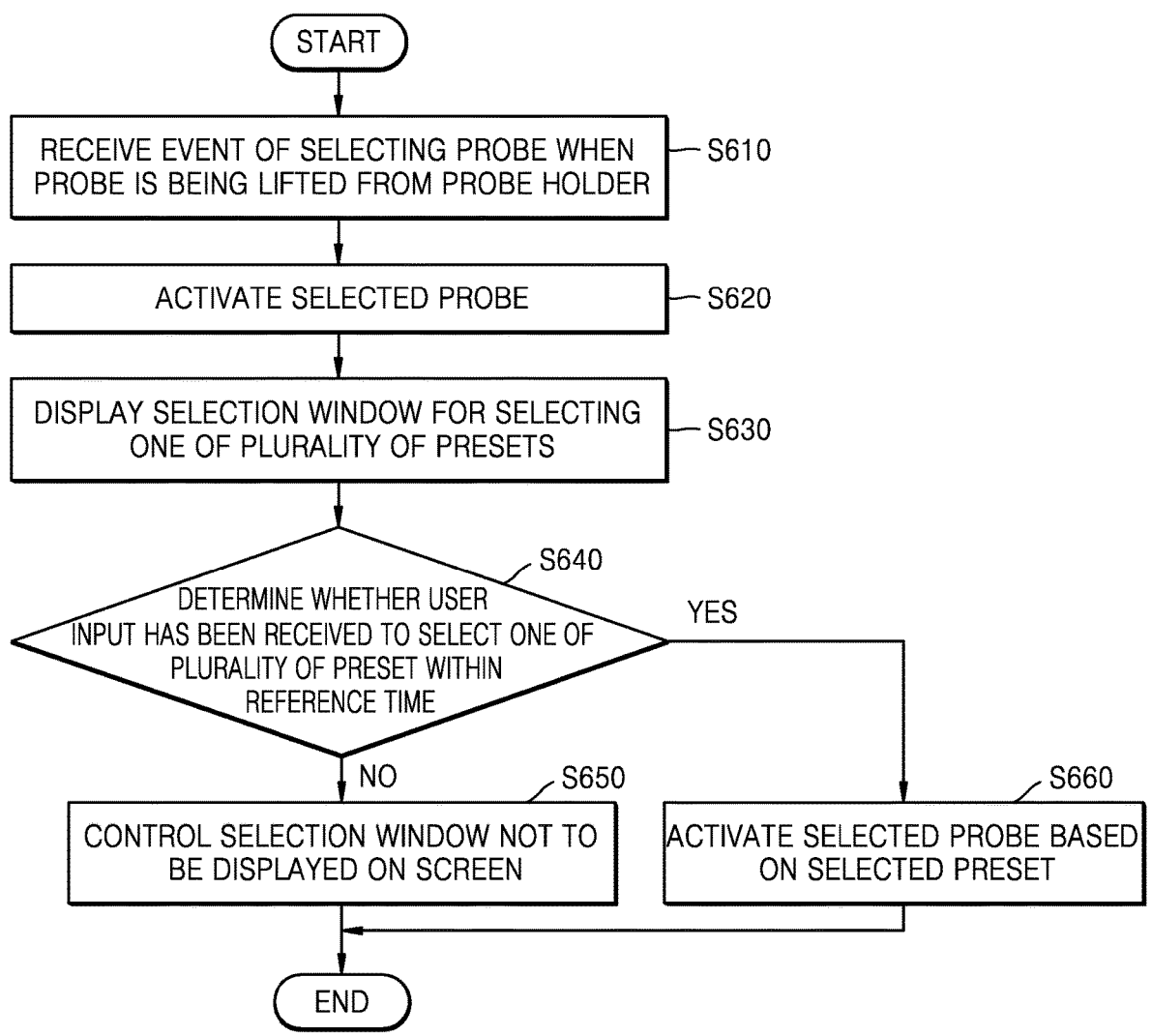
FIG. 6A is a flowchart illustrating the method in which the ultrasound imaging apparatus sets the imaging parameter depending on whether the user input to select the preset within a reference time is received according to an embodiment of the present invention.

FIG. 6A is a flowchart illustrating the method in which the ultrasound imaging apparatus sets the imaging parameter depending on whether the user input is received for selecting the preset within a reference time, according to an embodiment of the present invention.

In operation S610, the ultrasound imaging apparatus 1000 may detect a selection event in which the user removes the probe from the probe holder.

In operation S620, the ultrasound imaging apparatus 1000 may activate the selected probe.

In operation S630, the ultrasound imaging apparatus 1000 may display the selection window for selecting one of the presets.

In operation S640, the ultrasound imaging apparatus 1000 may determine whether the user input of selecting one of the presets has been received within a reference time.

In the case that the user input of changing the imaging probe or the imaging preset has not been received within a reference time at stage S640, the ultrasound imaging apparatus 1000 may hide the selection window 100 at stage S650.

In the case that the user input of selecting one of the presets has been received within a reference time at stage S640, the ultrasound imaging apparatus 1000 may activate the selected probe 20 based on the selected preset at stage S660.

Figure 6B:
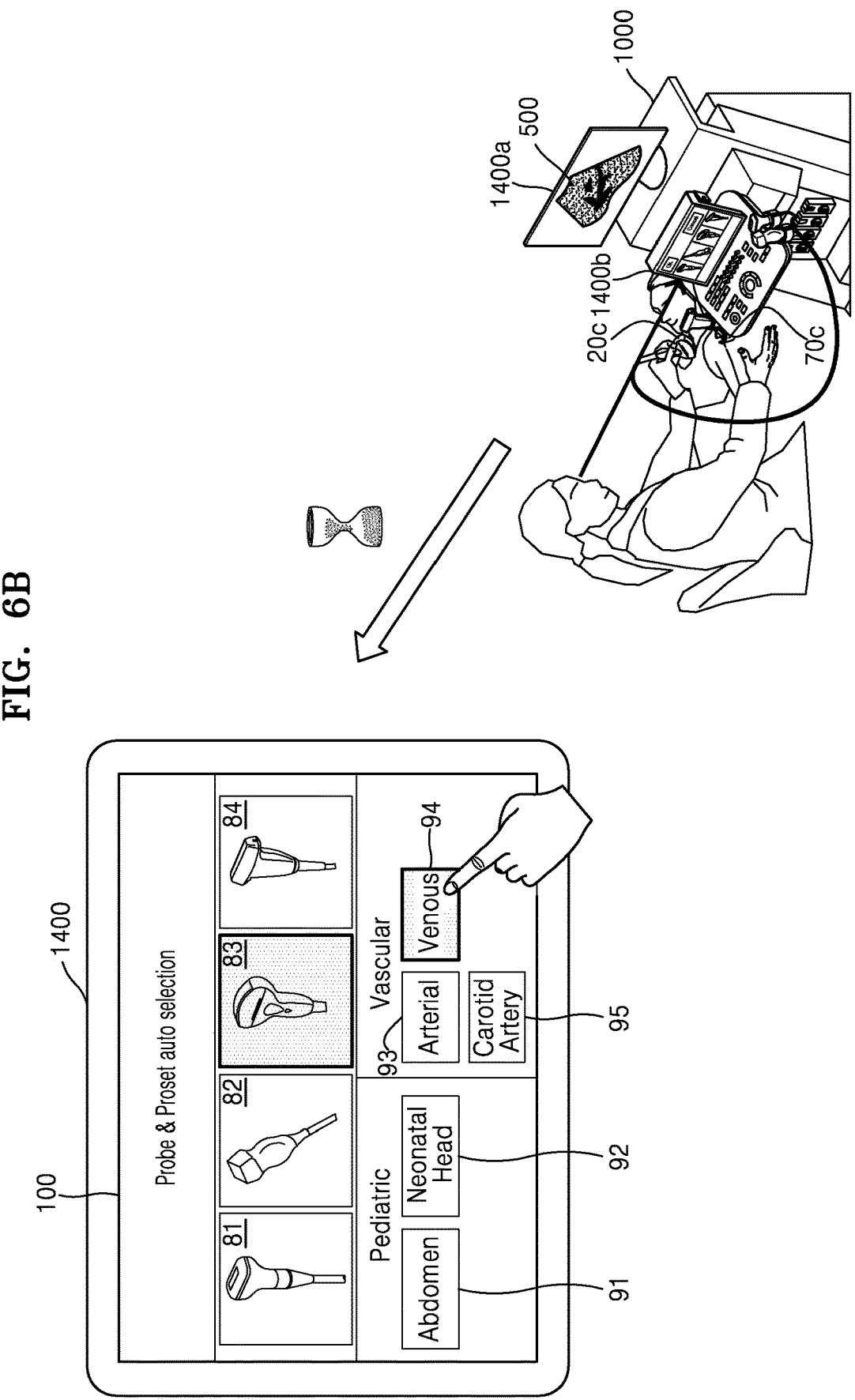
FIG. 6B is a view illustrating the method in which the ultrasound imaging apparatus sets the imaging parameter when the user input to select the preset within a reference time is received according to an embodiment of the present invention.

FIG. 6B is a view illustrating the method in which the ultrasound imaging apparatus may set the imaging parameter when the user input of selecting the preset is received within a reference time, according to an embodiment of the present invention.

Referring to FIG. 6B, in the case that the user input for changing the preset has been received, the ultrasound imaging apparatus 1000 may change the preset selected by the user to the imaging parameter. Further, the ultrasound imaging apparatus 1000 may transmit the ultrasound signal based on the changed imaging parameter and generate the ultrasound image again based on the received ultrasound echo signal.

For example, while the convex probe 20*c* is automatically set as the imaging probe, the ultrasound imaging apparatus 1000 may change the imaging parameter to the "Venous" preset, in the case that the user input for selecting the "Venous" preset selection button 94 is received within a reference time after "Carotid Artery" is automatically set as the imaging parameter. In some embodiments, the ultrasound imaging apparatus 1000 may generate the ultrasound image 500 again based on the changed parameter.

Figure 7A:
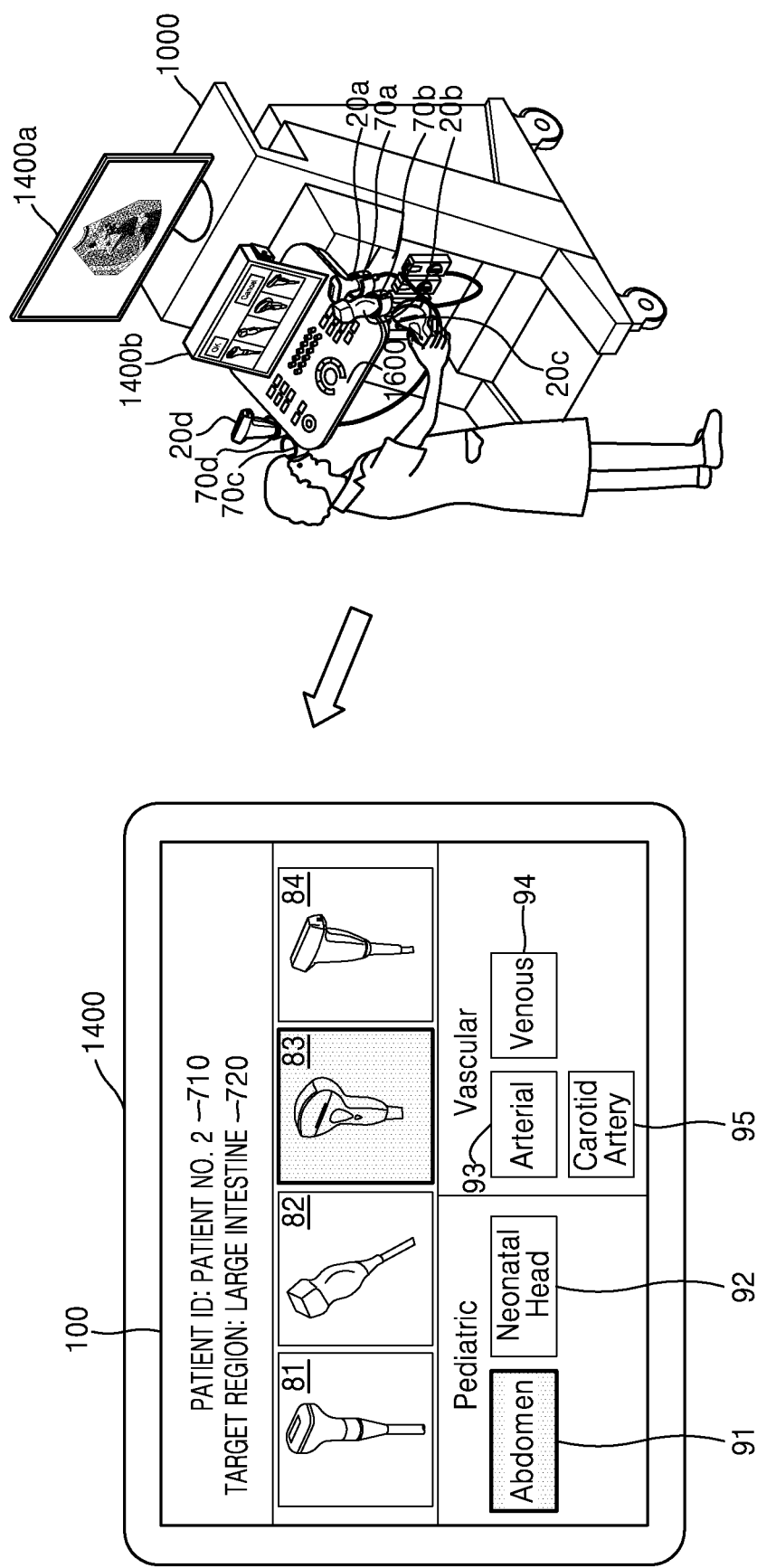

FIGS. 7A and 7B are views illustrating the method in which the ultrasound imaging apparatus 100 sets the imaging parameter based on the ID information of the object, according to an embodiment of the present invention.

Referring to FIG. 7A, the ultrasound imaging apparatus 1000 may set as the imaging parameter the default preset which corresponds to the selected probe 20 based on the ID information of the object.

The ultrasound imaging apparatus 1000 may receive information on the object. The object information may include information about a patient's ID, target region, predicted disorder, weight, sex and age. For example, the ultrasound imaging apparatus 1000 may receive the user input for setting the information regarding the object. In some embodiments, the ultrasound imaging apparatus 1000 may receive information regarding the object from an external device. In some embodiments, the ultrasound imaging apparatus 1000 may receive information regarding the object from a wireless communication (for example, short distance a wireless communication) terminal carried by the patient.

Referring to FIG. 7*b*, the ultrasound imaging apparatus 1000 may acquire the patient's ID 700 and the ID information 720 of the default preset which corresponds to the ID information 710 of the probe 20.

The ultrasound imaging apparatus 1000 may have saved the patient's ID 700 and the ID information 720 of the default preset which corresponds to the ID information 710 of the probe 20, which was selected as the imaging probe. For example, the ultrasound imaging apparatus 1000 may save the imaging parameter which has been used most recently for the patient as the default preset which corresponds to the patient's ID 700 and the imaging probe. In some embodiments, the ultrasound imaging apparatus 1000 may save the imaging parameter, which has been used most frequently for the patient during a certain period of time, as the default preset which corresponds to the patient's ID 700 and the imaging probe.

Therefore, upon receiving the user input for selecting the probe 20, the ultrasound imaging apparatus 1000 may select as the imaging parameter the default preset which corresponds to the selected probe 20 and the patient's ID. For example, as the patient's ID is entered as "Patient No. 2", and the user removes the Phased Array probe 20*a* from one of the probe holders 70, the ultrasound imaging apparatus 1000 may automatically set the Phased Array probe 20*a* as the imaging probe and automatically set "Liver", the default preset which corresponds to the patient's ID and the Phased Array probe 20*a*, as the imaging parameter.

Referring to FIG. 7C, the ultrasound imaging apparatus 1000 may acquire the ID information 780 of the default preset which corresponds to the target region 760 or the predicted disorder, and the ID information 770 of the probe 20. For example, the ultrasound imaging apparatus 1000 may have saved the ID information 780 of the default preset which corresponds to the target region 760 or the predicted disorder, and the ID information 770 of the probe 20.

Accordingly, the ultrasound imaging apparatus 1000 may select as the imaging preset the default preset which corresponds to the target region 760 or the predicted disorder, and the ID information 770 of the probe 20. For example, when the target region of a "patient" is his or her large intestine, upon receiving the user input for taking out the Phased Array probe 20*a* from one of the probe holders 70, the ultrasound imaging apparatus 1000 may automatically set the convex probe 20*c* as the imaging probe. In some embodiments, the ultrasound imaging apparatus 1000 may automatically set as the imaging preset the predetermined "Abdomen" preset which corresponds to the large intestine or colorectal cancer, and the convex probe 20*c*.

Figure 8:
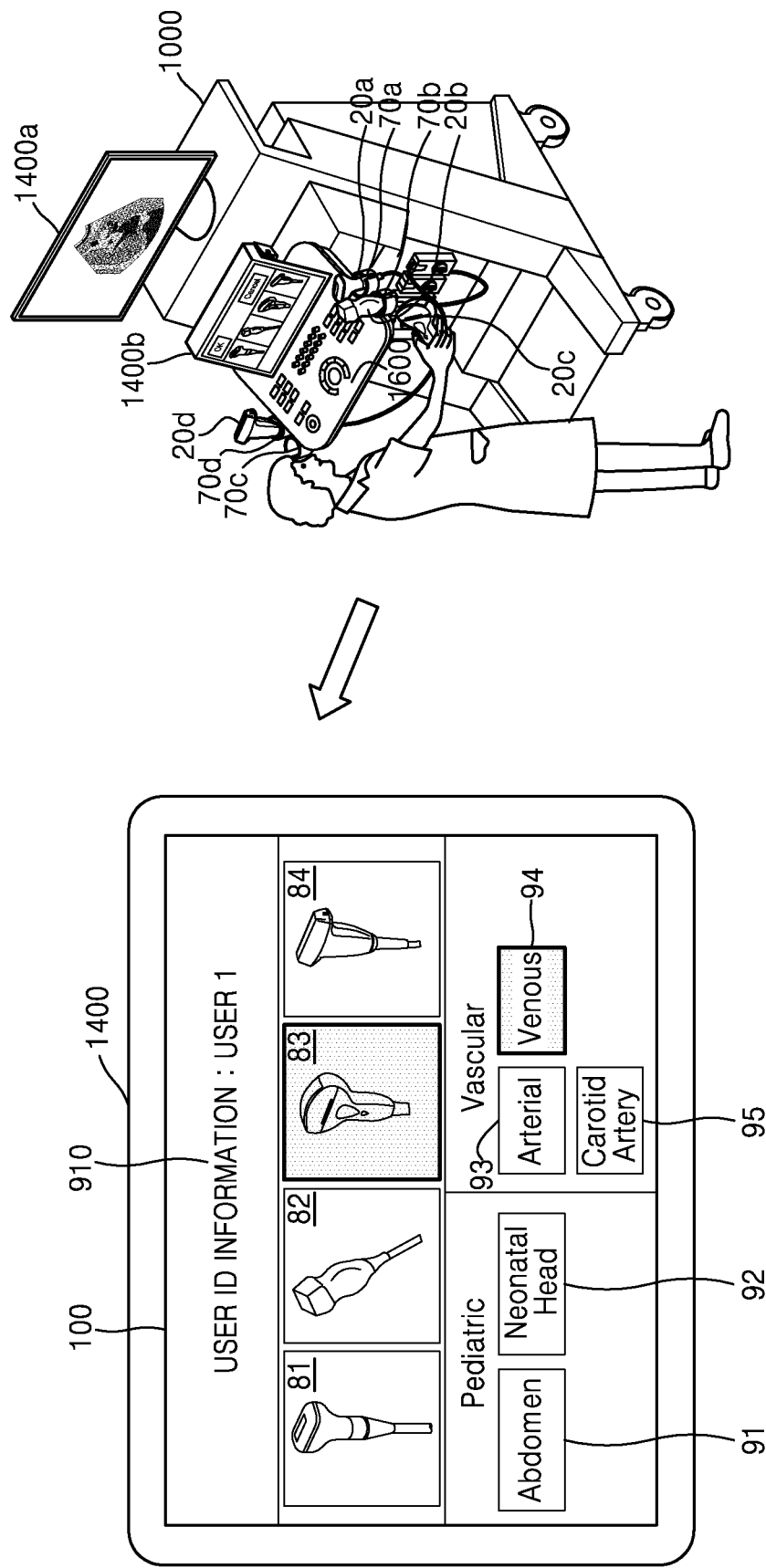
FIG. 8 is a view illustrating the method in which the ultrasound imaging apparatus sets the imaging parameter based on the ID information of the user according to an embodiment of the present invention.

FIG. 8 is a view illustrating the method in which the ultrasound imaging apparatus sets the imaging parameter based on the ID information of the user, according to an embodiment of the present invention.

Referring to FIG. 8, the ultrasound imaging apparatus 1000 may set as the imaging parameter the default preset which corresponds to the selected probe 20, based on the ID information of the user.

For example, the ultrasound imaging apparatus 1000 may receive various pieces of information regarding the user. Such information on the user may include the ID of the user.

For example, the ultrasound imaging apparatus 1000 may receive the user input for setting the information regarding the user. In some embodiments, the ultrasound imaging apparatus 1000 may receive the information regarding the user from the external device. In some embodiments, the ultrasound imaging apparatus 1000 may receive the information regarding the user from the wireless communication terminal carried by the patient.

The ultrasound imaging apparatus 1000 may acquire the default preset on each of the probes 20a-20d, in correspondence to the ID information of the user. For example, the default preset on each of the probes 20a-20d, corresponding to the ID information of the user, may be saved on the ultrasound imaging apparatus 1000.

Upon detecting the user's motion of removing one of the probes 20a-20d, the ultrasound imaging apparatus 1000 may automatically set as the imaging parameter the default preset which corresponds to the detected probe 20.

Figure 9:
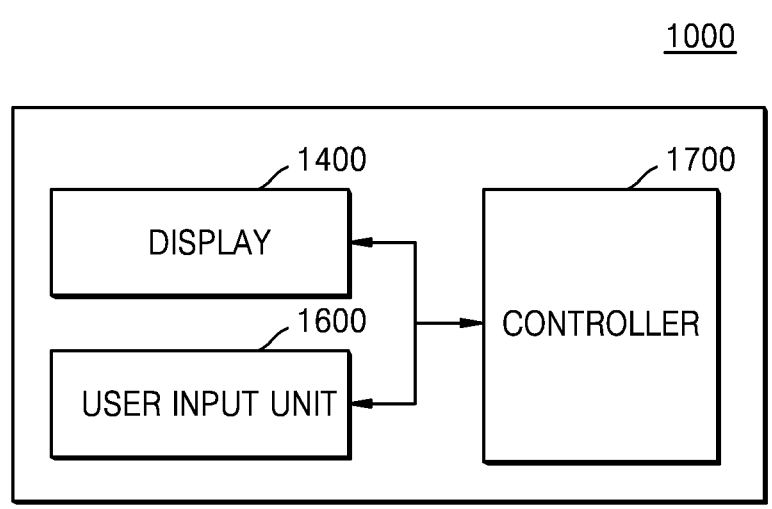
FIG. 9 is a block diagram of the ultrasound imaging apparatus according to an embodiment of the present invention.

FIG. 9 is a block diagram of the ultrasound imaging apparatus 1000 according to an embodiment of the present invention.

Referring to FIG. 9, the ultrasound imaging apparatus 1000 may include a display 1400, an user input unit 1600, and a controller 1700.

The user input unit 1600 may receive the user input for selecting one of the probes. In some embodiments, the user input unit 1600 may receive the user input for selecting one of the presets.

In some embodiments, the user input unit 1600 may include a sensor unit (not shown) which detects the user input of taking out the probe from the probe holder. In some embodiments, the user input unit 1600 may receive the user input for selecting the probe by using the sensor unit.

The controller 1700 may activate the selected probe, based on the default preset which corresponds to the selected probe among the presets corresponding to the selected probe.

In some embodiments, the controller 1700 may determine whether the user input has been received to select one of the presets within a reference time.

In some embodiments, the controller 1700 may control the display to make the selection window invisible from the screen in the case that the user input has not been received for selecting one of the presets within a reference time.

In some embodiments, in the case that the user input has been received for selecting one of the presets within a reference time, the controller 1700 may activate the probe based on the selected preset.

In some embodiments, upon activating the selected probe, the controller 1700 may generate the ultrasound image based on the echo signal which is received through the probe.

The display 1400 may display the selection window for selecting one of the presets.

In some embodiments, the display 1400 may display the generated ultrasound image.

In some embodiments, the display 1400 may indicate in the selection window that the selected probe and default preset have been selected.

Figure 10:
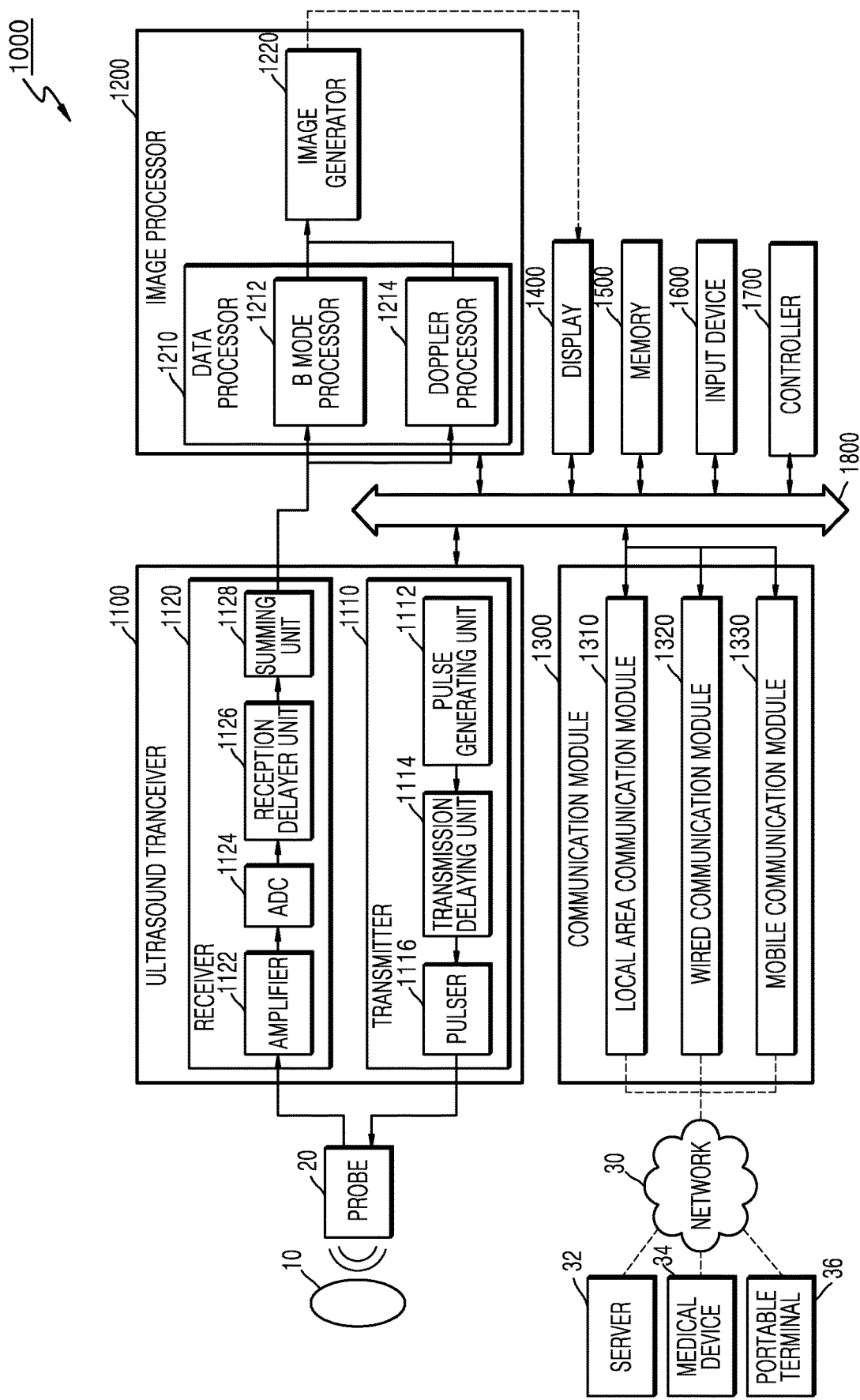
FIG. 10 is a block diagram of the configuration of the ultrasound imaging apparatus related to an embodiment of the present invention.

FIG. 10 is a block diagram of the configuration of the ultrasound imaging apparatus related to an embodiment of the present invention.

According to an embodiment of the present invention, the ultrasound imaging apparatus 1000 may include the probes 20, an ultrasound transceiver 1100, an image processor 1200, a communication module 1300 and a memory 1500, in addition to the display 1400, the user input unit 1600 and the controller 1700. The aforementioned components may be connected to one another via a bus 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly. According to embodiments of the present invention, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator

1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments of the present invention.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, embodiments of the present invention are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 1.

All or some of the probe 20, the ultrasound transceiver 1100, the image processor 1200, the communication module 1300, the display 1400, the memory 1500, the input device 1600, and the controller 1700 may be implemented as software modules. However, embodiments of the present invention are not limited thereto, and some of the components stated above may be implemented as hardware modules. Furthermore, at least one selected from the ultrasound transceiver 1100, the image processor 1200, and the communication module 1300 may be included in the controller 1600. However, embodiments of the present invention are not limited thereto.

The method according to an embodiment of the present invention may be implemented in program command formats which may be executed by various computing devices. Therefore, the method may be recorded in computer-readable media. The aforementioned computer-readable media may include program commands, data files, and data configurations individually or in combination. The program commands may be designed and configured specifically for the present invention, or widely known and available to those of ordinary skill in the art of computer software. Examples of the computer-readable media may include magnetic media such as a hard disk, a floppy disk and a magnetic tape, optical media such as a CD-ROM and a DVD, magneto-optical media such as a floptical disk, and hardware devices which are especially configured to save and execute program commands such as ROM, RAM, and flash memory. Examples of the program commands may include a machine language code made by a compiler and a high-level language code executable by a computer using an interpreter, and the like.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. A method of setting an ultrasound preset in an ultrasound imaging apparatus, the method comprising:
    obtaining an event which indicates that a selected probe has been removed from a probe holder;
    displaying, on a screen, a selection window for selecting a preset corresponding to the selected probe based on the event, wherein the selection window includes a first identifier indicating the selected probe and a second identifier indicating a default preset corresponding to the selected probe from among a plurality of presets, wherein the plurality of presets indicate information of a plurality of pre-stored parameters, which are used in ultrasound imaging in the ultrasound imaging apparatus;
    selecting the default preset which is automatically set as an imaging parameter when a user input selecting a preset corresponding to the selected probe from among the plurality of presets is not entered within a reference time; and
    hiding the selection window.

2. The method of claim 1, wherein the reference time is set to a default value and is changeable by a user.

3. The method of claim 1, further comprising, when a user input selecting a first preset corresponding to the selected probe from among the plurality of presets is entered within the reference time, activating the selected probe based on the first preset.

4. The method of claim 1, further comprising
    activating the selected probe by applying the default preset to the selected probe.

5. The method of claim 4, further comprising
    generating an ultrasound image based on an echo signal received through the selected probe when the selected probe is activated, and
    displaying the generated ultrasound image.

6. The method of claim 1, wherein the default preset is a preset which was most recently used for the selected probe.

7. The method of claim 1, wherein the default preset is a preset which is used most frequently for the selected probe from among the plurality of presets.

8. The method of claim 1, wherein the default preset is a preset which has already been predetermined by a user for the selected probe.

9. The method of claim 1, wherein the default preset is a preset which corresponds to identifiable information about an object.

10. The method of claim 1, wherein the default preset is a preset which corresponds to identifiable information about a user.

11. An ultrasound imaging apparatus which:
    obtains an event which indicates that a selected probe has been removed from a probe holder;
    displays a selection window on a screen for selecting a preset corresponding to the selected probe based on the event, wherein the selection window includes a first identifier indicating a selected probe and a second identifier indicating a default preset corresponding to the selected probe from among a plurality of presets, wherein the plurality of presets indicate information of a plurality of pre-stored parameters, which are used in ultrasound imaging in the ultrasound imaging apparatus;
    selects the default preset which is automatically set as an imaging parameter in the case a user input for selecting a preset corresponding to the selected probe from among the plurality of presets is not entered within a reference time; and
    hides the selection window.

12. The ultrasound imaging apparatus of claim 11, wherein the reference time is set by default and is changeable by a user.

13. The ultrasound imaging apparatus of claim 11, wherein the ultrasound imaging apparatus comprises a user input unit and a controller,
    wherein the user input unit receives a user input to select a first preset from among the plurality of presets within a reference time, and
    the controller activates the selected probe, based on the first preset upon receiving the user input to select the first preset within a reference time.

14. The ultrasound imaging apparatus of claim 13, wherein the control unit activates the selected probe by applying the default preset to the selected probe.

15. The ultrasound imaging apparatus of claim 14, further comprising a display unit,
    wherein the control unit generates an ultrasound image based on an echo signal received through the probe when the selected probe is activated, and
    the display unit displays the generated ultrasound image.

16. The ultrasound imaging apparatus of claim 11, wherein the default preset is a preset that was most recently used for the selected probe.

17. The ultrasound imaging apparatus of claim 11, wherein the default preset is a preset which is used most frequently for the selected probe.

18. The ultrasound imaging apparatus of claim 11, wherein the default preset is a preset which has already been predetermined by a user for the selected probe.

19. The ultrasound imaging apparatus of claim 11, wherein the default preset is a preset which corresponds to the ID information of an object.

20. The ultrasound imaging apparatus of claim 11, wherein the default preset is a preset which corresponds to the ID information of a user.

* * * * *